(12) United States Patent
Sivak

(10) Patent No.: US 6,421,119 B1
(45) Date of Patent: Jul. 16, 2002

(54) IN VITRO EVALUATION OF ANIMAL OR HUMAN LENS CHARACTERISTICS

(75) Inventor: Jacob G. Sivak, Waterloo (CA)

(73) Assignee: XTOX Scientific Inc., Nepean (CA)

( * ) Notice: Subject to any disclaimer, the term of this patent is extended or adjusted under 35 U.S.C. 154(b) by 0 days.

(21) Appl. No.: 09/276,638

(22) Filed: Mar. 26, 1999

(51) Int. Cl.$^7$ ............................................... G01B 9/00
(52) U.S. Cl. ..................................................... 356/125
(58) Field of Search ................................. 356/124–127

(56) References Cited

U.S. PATENT DOCUMENTS

| 4,832,486 A | 5/1989 | Gershon et al. |
| 4,865,985 A | 9/1989 | Sivak et al. |

OTHER PUBLICATIONS

Sivak et al.: "In Vitro Ocular Irritancy Measure of Four Contact Lens Solutions: Damage and Recovery". *The CLAO Journal*, Jul. 1995, vol. 21, No. 3: 169–174.

Dovrat A., Weinreb O.: "Recovery of Lens Optics and Epithelial Enzymes After Ultraviolet A Radiation". *Investigative Ophthalmology & Visual Science*, Nov. 1995, vol. 36, No. 12: 2417–2424.

Sivak J.G., Herbert K.L. "Optical Damage and Recovery of the In Vitro Bovine Ocular Lens for Alcohols, Surfactants, Acetates, Ketones, Aromatics, and Some Consumer Products: A Review". *J. Toxicol.—Cut. & Toxicol.*, 1997, 16(3):173–187.

Hartwick, et al "Relative Toxicity of Three Corneal Anesthetics Measured In Vitro with the Cultured Bovine Lens". *J. Toxicol—Cut. & Toxicol.*, 1997, 16(4): 253–266.

Herbert, et al "Effects of Age on the Sensitivity of the Rat Lens to Hexanol In Vitro". *J. Toxicol.—Cut & Ocular Toxicol.*, 1998, 17 (2&3): 127–139.

Bantseev, et al "Laser Scanning Focal Length Variability is a Measure of Damage in Rat Lens in Model Astronaut Cataracts Treated with Vitamin E (VE) or R– –Lipoic Acid (RLA)," *NATO Advance Study Workshop—Ocular Radiation Risk Assessment in Populations Exposed to Environmental Radiation Contamination*, 1998, pp. 1–10.

*Primary Examiner*—Frank G. Font
*Assistant Examiner*—Amanda Merlino
(74) *Attorney, Agent, or Firm*—R. Craig Armstrong

(57) ABSTRACT

An improved apparatus and method for evaluation of focal length and transparency of vertebrate eye lenses is provided. Preferably with the aid of an alignment camera, a lens horizontally mounted in a transparent container is positioned with the axis of the lens aligned with scanning direction of a laser projected vertically through the lens. The laser is scanned across the lens, and an analysis camera at ninety degrees to the scanning path captures images of the path of the laser beam through the lens. The images are then analysed for determination of focal length, spherical aberration, and the like. Changes over time in response to a stimulus may be evaluated.

12 Claims, 8 Drawing Sheets

Beam Image

IN VITRO EVALUATION OF ANIMAL OR HUMAN LENS CHARACTERISTICS

BACKGROUND OF THE INVENTION

1. Field of the Invention

This invention relates to an improved method and apparatus for evaluating focal characteristics and focal characteristic changes in ocular lenses of humans and animals in an in vitro culture.

The improved apparatus measures focal length, focal length variance and transparency of a given lens, and can be used to measure changes in these focal characteristics over time, for example in response to exposure to various irritants.

2. Description of the Prior Art

For many years, research interest has focussed on the examination of optical characteristics of lenses and the biology of aging of the lens. Meaningful examination of the lenses requires that the lens be examined intact so as to preserve the ocular integrity of the lens. In order to assess risk associated with lens exposure to various chemical products and environmental agents, an in vivo testing procedure was introduced, known as the Draize test. The procedure involved placing test material on the eyes of live animals (preferably albino rabbits), and evaluating ensuing ocular damage at varying subsequent intervals. The Draize test procedure has been criticized due to the subjective nature of the evaluation of tissue damage, and the uncertainty of the results. Also, since little is known about differences in chemical sensitivity as the eye ages, such irritability testing may be inaccurate. Additionally, animal rights advocates have been concerned with the pain and suffering endured by the test animals as a result of Draize testing. This extensive criticism has led to exploration of alternative methods which attempt to measure in vivo lens damage. Intact lenses cultured in vitro have been shown to maintain in vivo function of light passage and refraction. Therefore, in vitro examination of intact cultured lenses has been a focus of alternative methods of lens testing.

Lenses refract light from a point source some distance from the lens onto a focal plane behind the lens. A perfect lens will focus light directed from an infinite distance to a single point, defined as the focal point. If however a living lens is exposed to a toxicological agent, i.e. any substance which causes the surface of the lens or the interior of the lens to react to the substance, the shape, surface and/or interior quality of the lens will change. Because of the structure of the living lens, the effect of these disturbances varies at different locations across the width of the lens. The result is that the focal length (for example, the distance from the rear surface of the lens to the focal point), at each location across the lens will vary, i.e. there is increased focal length variability (essentially spherical aberration) of the lens. If the agent is removed from the lens and the lens is nurtured in growth medium, it is possible that the lens will attempt to repair itself. In some cases, given enough time, the lens will return to its original condition or close to it. By repeatedly measuring the focal length at points across the diameter of a lens as an agent is introduced and then removed, it is possible to quantify lens damage and recovery over time. Moreover, by using this type of measurement, comparative results can be obtained between different types and concentrations of agents.

In addition to focal length variability, it has also been shown that irritability of cultured lenses to chemical stimuli can be reliably evaluated by measuring lens scatter and thus lens transparency.

The use of a scanning laser to assess changes in lens characteristics is known. U.S. Pat. No. 4,832,486 (Gershon et al., including the present inventor) describes the use of an x-y table to scan the laser across the lens in two directions, the lens being positioned in a special container. The resulting light path images are analyzed via a complex process to determine focal length and focal length variability (spherical aberration).

Although this prior art method and apparatus have been effective in their study of ocular characteristics of intact lenses, there are certain deficiencies which have become evident through their use. Therefore, various improvements to the apparatus and the method to use same are desirable in order to allow for more accurate, reliable and less cumbersome measurements of lens focal characteristics and thus the study of lens pathology. In particular, it is highly desirable to avoid the complexities associated with scanning across the lens in two directions.

In the Gershon et al. patent, the lens optical axis is determined by locating the optical center position on the lens through which a laser beam incurs the minimal refraction. The optical center is located iteratively by scanning the laser through the lens at various positions on the x and y planes of the lens, moving the laser progressively closer in smaller steps until the beam passes through the lens without deviation. Two cameras are required for the analysis, i.e. one to look at the x-axis motion and one to look at the y-axis motion. Once the optical axis is determined, equivalent focal length is then measured by projecting the beam through the lens at various positions along the lens, in a plane passing through the optical axis. A more efficient means to determine the optical axis than this multi-step process is required.

Equivalent focal length is typically measured as the distance from the principal plane within the lens (the intercept of the incoming beam with the exiting beam) to the intercept of the beam to the optical axis. Any variation in focal length at different positions along the lens is influenced predominantly by spherical aberration, however the presence of coma in the lens is also a factor. In order to better determine focal length variability caused by spherical aberration rather than coma, a more reliable measurement is required.

Additionally, the Gershon et al. patent used a laser in which entails the beam which is slightly oval in cross section, making it difficult to equate video beam thresholds (width and brightness) in the two directions. An improved method involving unidirectional laser movement is preferred.

In addition to measuring refractive conditions of the lens, such scanning laser systems attempt to measure lens scatter (transparency of the lens) for each laser position. However, scatter measurements have proven to be difficult to interpret in comparison to focal measurements and therefore have not been utilized to determine lens health. An effective means to present and evaluate lens transparency information is required.

Improvements to the lens containers are also desirable. The Gershon et al. lens container, described in the above-mentioned patent and more thoroughly in U.S. Pat. No. 4,865,985 also by Gershon et al., has shown some problems with leakage of the medium in which the lens must sit to be scanned by the lens. The prior container also did not permit observation of the rear surface of the lens. Therefore an improved lens container is also desired as part of the overall system.

SUMMARY OF THE INVENTION

It is an object of the invention to provide an improved method and apparatus for determining lens focal length, evaluation of spherical aberration of the lens, and measurement and analysis of lens transparency, and a method of comparison of these measurements over time.

In particular, it is an object of the invention to avoid the use of an x-y table, and to avoid the need for analysing data from two cameras.

In the invention, therefore, although a second camera is used for the purpose of roughly aligning the scanning laser with the lens axis, the laser is scanned in only one dimension, and data from scanning is collected from only one camera. This greatly simplifies the apparatus and the method, and speeds up the process considerably.

In the invention, a vertebrate eye lens sits horizontally in a culture medium within a transparent lens container within an area for viewing the lens. The laser is directed upwardly through the lens, for scanning across the x direction. With the aid of an alignment camera facing the lens in the x direction, the position of the platform on which the lens container is carried is manually adjusted in the y direction so that the laser is aligned approximately with the lens axis in the y direction. An analysis camera is directed at the lens normal to the lens optical axis, for viewing the lens, and the path of the laser beam after it exits the lens. The laser beam is translated in the x direction, preferably by moving a mirror on a carriage, to direct the laser beam through the container and the lens, parallel to the lens axis at a plurality of locations along the x axis. The analysis camera captures the images of the beams at the plurality of locations, for computer analysis.

A means for rotating the lens and lens container in relation to the translational path of the laser beam is also provided so that multiple axes of the lens can be scanned, if desired. A means for recording data received from the analysis camera image and a means for analysis of that recorded data for determination of focal length, and lens transparency is also provided.

In contrast to the previously-mentioned Gershon et al. patent, the laser in the invention is scanned in one direction only. The lens is manually centered relative to the laser beam, preferably with the aid of an alignment camera.

As the laser beam path is analysed, the invention preferably also provides an effective simultaneous measurement of light intensity of each refracted beam, and thus an indicator of lens scatter (transparency) at various positions along the lens.

In the analysis of the images captured by the analysis camera, focal length at various positions along the lens is calculated using back vertex distance, that being the distance from the back vertex position to the focal point. Back vertex distance, i.e. the distance from the rear surface of the lens to the focal point, has been found by the inventor to be a preferable measurement over equivalent focal length since any discrepancy in back vertex distance is due solely to spherical aberration, rather than possibly due to coma.

To achieve first the desired alignment and then the desired measurements, the lens laser interface must be visible to the cameras. Thus the container in which the lens sits presents the lens to the cameras such that back vertex of the lens and the lens focal area (the area between the lens focal point and the lens) are viewable by the cameras, which was not the case with the previous Gershon et al. container.

The apparatus therefore uses an upright lens container, having transparent side walls extending upwardly from a base unit, the base unit having a transparent central portion at its bottom. The lens is supported upon a lens carrier unit and a lens holding washer, such that the lens will be exposed to a laser beam projected through this central portion, through the bottom of the container. The container base unit is attached to the sidewalls by means of a detachable liquid-tight seal. The container is oriented such that the laser beam can be sent through the bottom transparent portion and then the lens, parallel to the lens optical axis.

Within the container, the lens support unit preferably comprises corner posts extending upwardly from the base unit, for support of the lens holding washer. The lens holding washer is designed to sit on the corner posts, with the lens being supported peripherally by the lens holding washer. The side walls must extend at least as high as the largest focal area of subject lenses so that the entire focal area will be contained within the container and thus the relevant laser beam path can be viewed in the culture medium by the cameras.

The side walls of the container are flat-surfaced, in order to minimize the refraction effects while looking through the side of the container. The base of the container is sized and configured to sit on a sliding platform which sits upon the laser scanner apparatus.

The invention also provides a method for evaluating focal length, spherical aberration and lens transparency using the above apparatus. An intact vertebrate lens is positioned in a culture medium within the transparent lens container. Preferably, the lens and the container are positioned for viewing by two digital cameras, namely an alignment camera for aligning the lens relative to the laser beam, and an analysis camera at ninety degrees to the alignment camera, for viewing the lens and laser beam path and intensity. The laser beam is projected from below the container, through the central transparent portion. The alignment camera displays an image of the lens in the x direction, and the platform position is then manually moved in the y direction via an alignment knob, to approximately align the laser beam with the lens axis (as observed by straight-through passage of the beam). The laser beam is then scanned across lens in the x direction, at a plurality of positions along the lens. The analysis camera views and captures the intensity and directional path of the laser beam as it passes through the culture medium, locating the back vertex location of the lens (by determining the point of maximum brightness) and the subsequent path of the laser beam, at the various positions along the lens. The information captured by the analysis camera is analysed to determine back vertex distance, focal length, focal length variance and transparency of the lens.

As in the prior art, a stimulus may be applied to the lens in the culture medium, and the above steps may be repeated after some elapsed time period, with the focal length, focal length variance (spherical aberration) and transparency of the lens before and after that period of time being compared, so as to determine the irritancy of the lens in response to the stimulus.

The invention further provides computer software which processes the images captured by the analysis camera to determine back vertex location at various locations on the lens, focal length at each location relative to the back vertex, the average focal length for the lens and standard deviation and error of the lens focal length. Similar results for the relative intensity of the beam are also calculated by the software program.

Further features of the invention will be described or will become apparent in the course of the following detailed description.

BRIEF DESCRIPTION OF THE DRAWINGS

In order that the invention may be more clearly understood, the preferred embodiment thereof will now be described in detail by way of example, with reference to the accompanying drawings, in which.

DETAILED DESCRIPTION OF THE PREFERRED EMBODIMENT

The preferred method of the present invention may be best understood in conjunction with the following description of the preferred embodiment of the apparatus used for carrying out the method.

Figure 1:
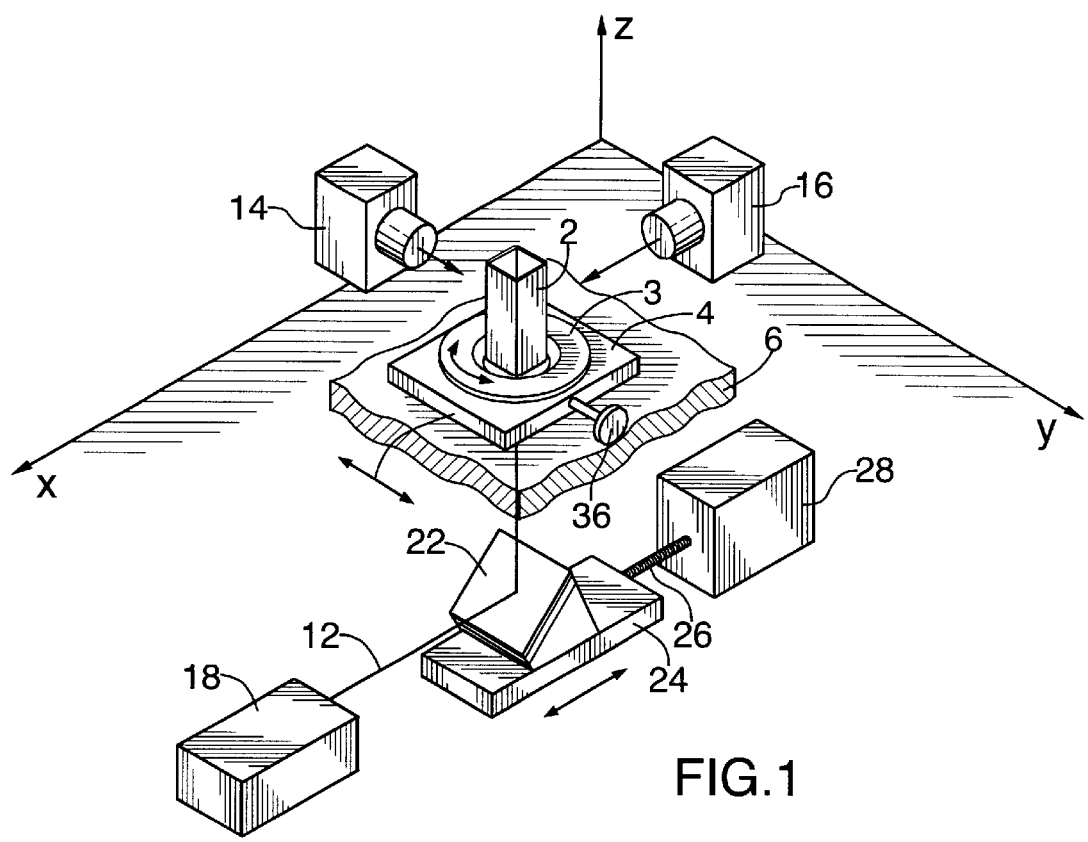
FIG. 1 is a schematic perspective of the preferred apparatus.
Figures 2A, 2B:
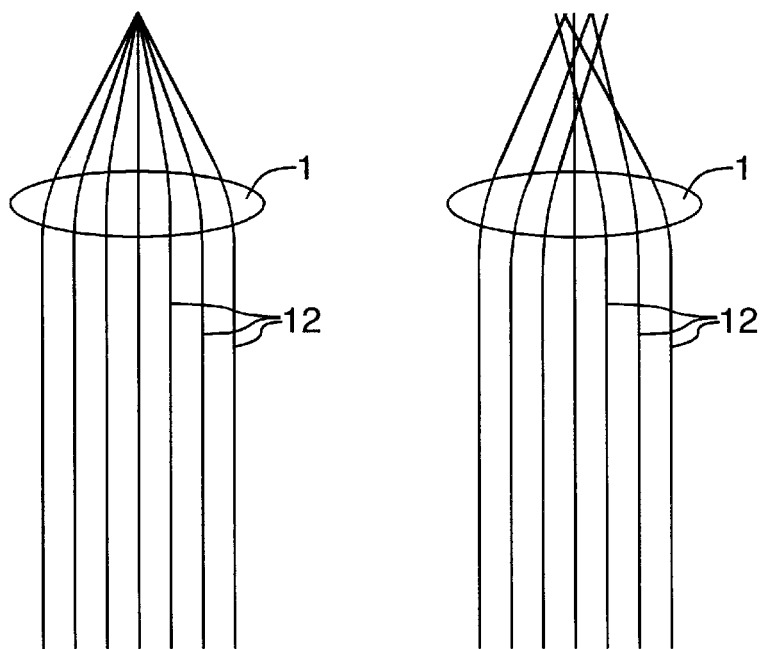
FIG. 2A is a schematic illustration of multiple beams projected through a perfect lens.
FIG. 2B is a corresponding sketch for an imperfect lens.
Figure 3:
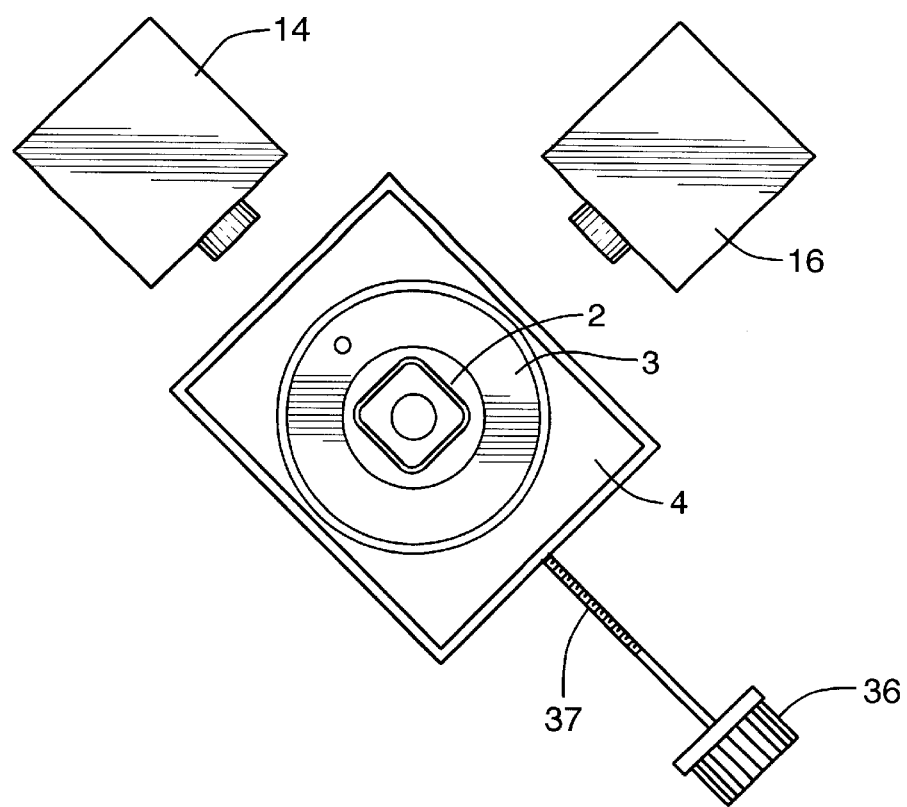
FIG. 3 is a schematic top view of the preferred embodiment of the apparatus.
Figure 4:
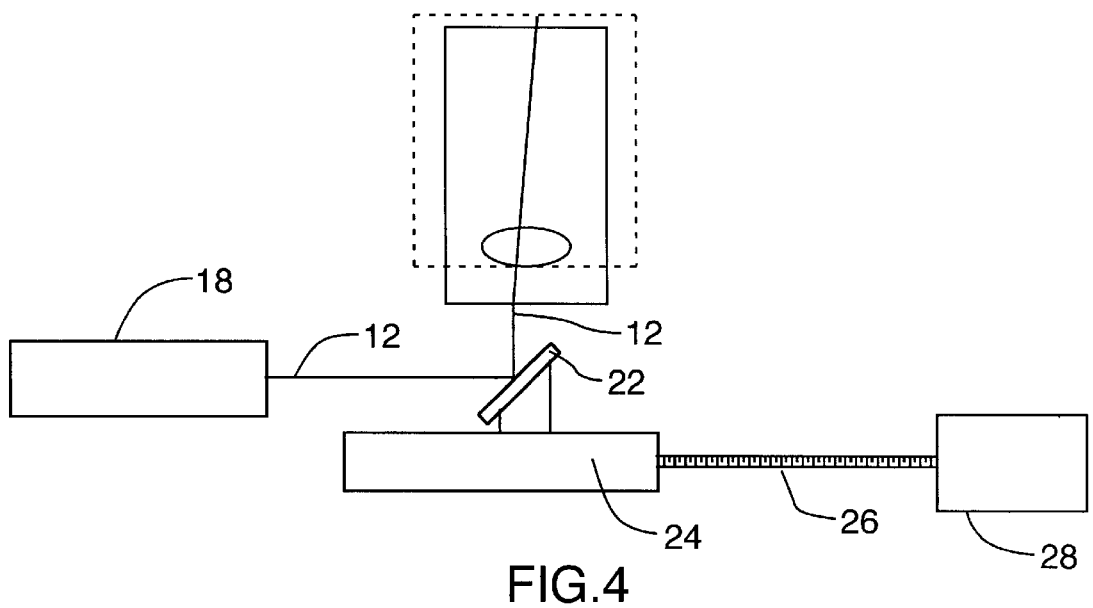
FIG. 4 is a schematic side view of the preferred embodiment of the apparatus.
Figure 5:
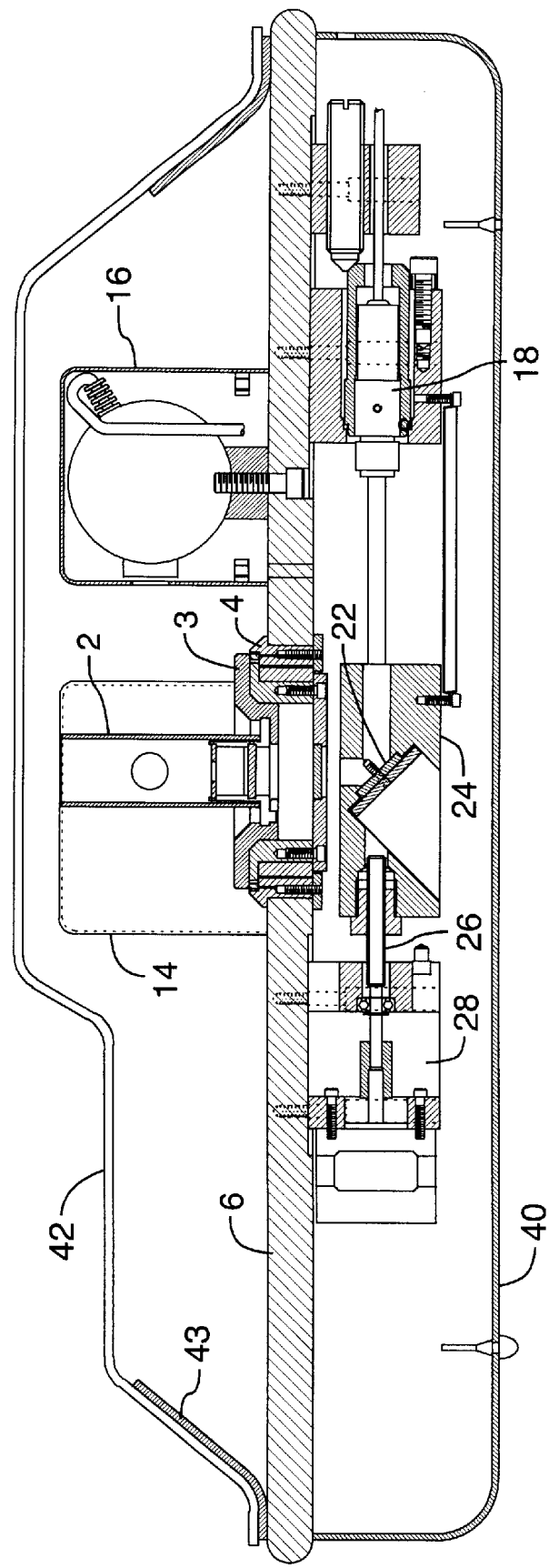
FIG. 5 is a detailed side view of the preferred embodiment of the apparatus.
Figure 6:
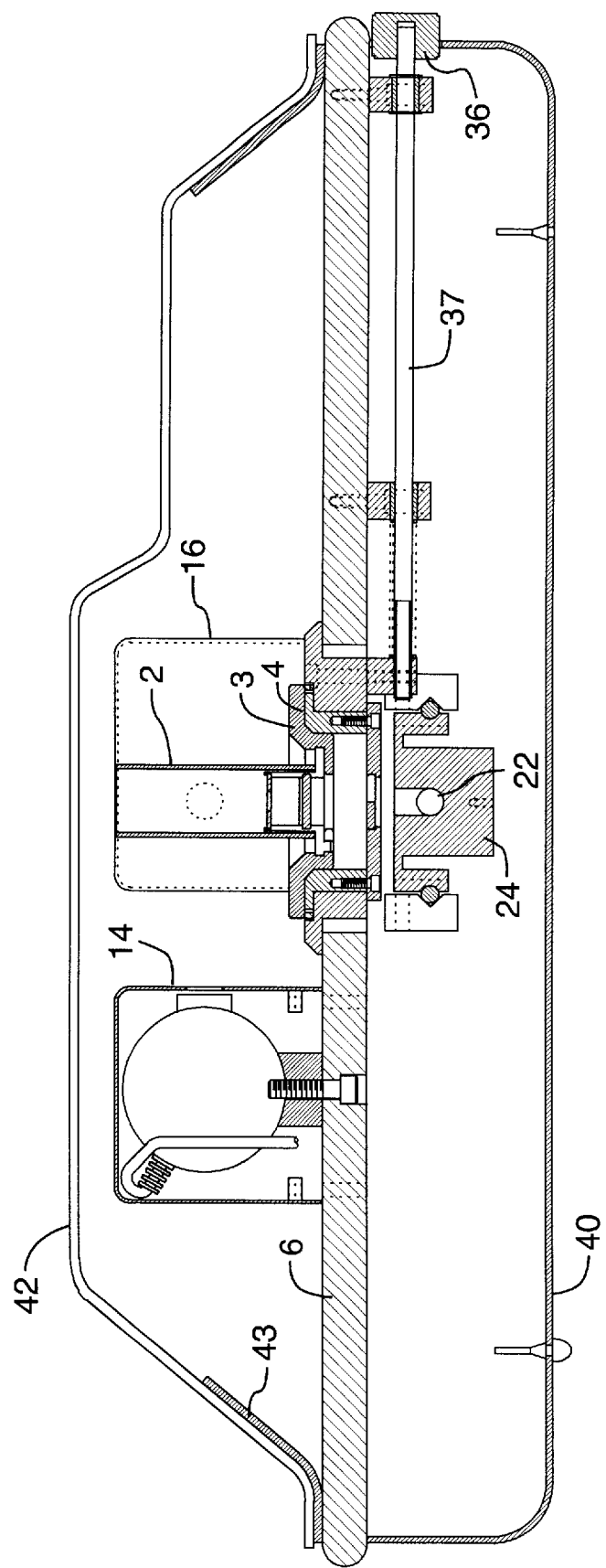
FIG. 6. is a detailed side view at ninety degrees to FIG. 5.
Figure 7:
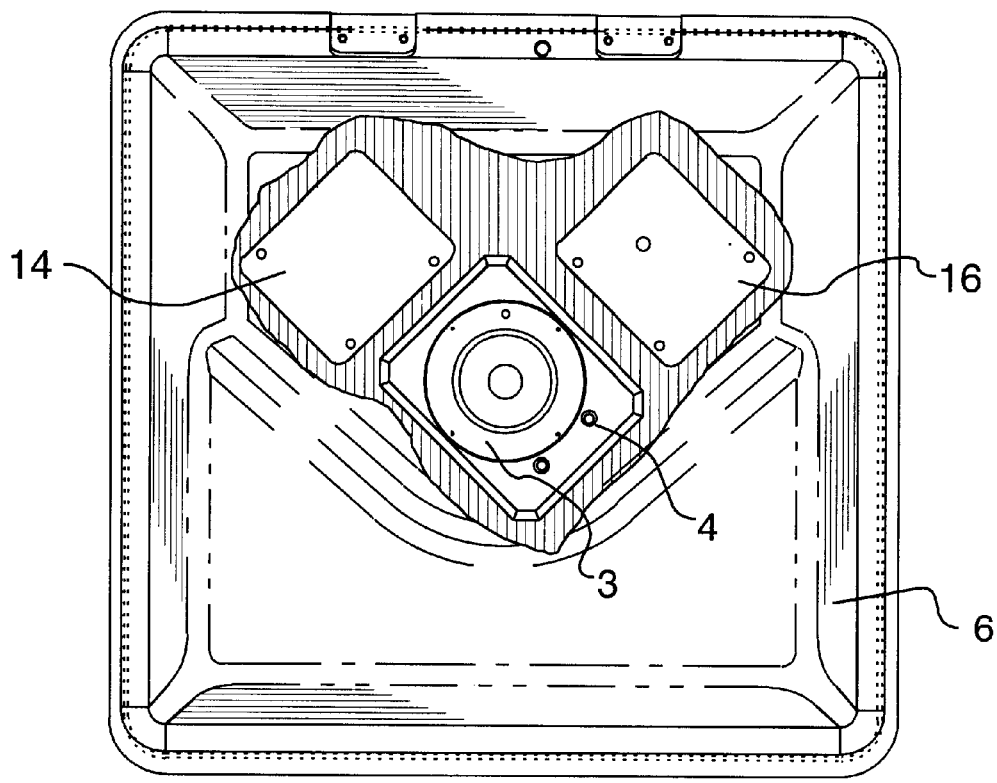
FIG. 7 is a detailed top view of the apparatus, showing the case containing the apparatus.
Figure 8:
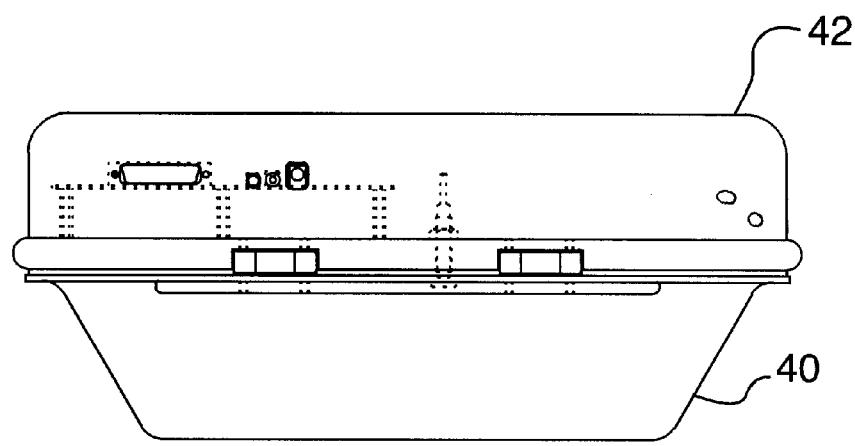
FIG. 8 is a side view of the case.

As illustrated schematically in FIG. 1, a transparent lens container 2 carrying a vertebrate eye lens 1 is mounted on a turntable 3 on a platform 4 which sits upon a support surface 6 and is slidable in the y direction via adjustment knob 36 which rotates a lead screw 37. The lens container will be described in greater detail later, but essentially it carries a lens horizontally, i.e. with the lens axis vertical, within a culture medium. A laser 18 projects a beam 12, which is reflected upwardly through the bottom of the container and thence through the lens by a mirror 22. The mirror is mounted on a sliding carriage 24, which is movable in the x direction via a drive screw 26 driven by a motor 28, such that this movement causes the laser beam to travel across the lens in the x direction. Before the motor 28 is operated to step or scan the laser beam across the lens in the x direction, the lens is aligned manually via the adjustment knob 36, so that the path of the laser beam will be approximately through the lens axis. Preferably this alignment is with the assistance of an alignment camera 16 looking at the container in the x direction, which produces an image of the laser beam passing through the lens. Proper alignment is indicated when the laser beam passes straight through the lens from that vantage point, rather than being deviated by the lens. Alternatively, the alignment could be done visually, but the alignment camera simplifies this task and avoids parallax errors.

Once the lens is properly aligned, the laser beam is scanned or stepped across the lens in the x direction by operation of the motor 28. The images of the beams are captured by an analysis camera 14 which looks at the container in the y direction. As the laser is stepped across the diameter of the lens, the refraction of the beam is clearly visible within the container, since the culture medium suspends fine particles which are illuminated by the laser beam. Analysis of the data will be discussed in greater detail later below.

Although the laser 18 could be positioned directly under the lens container to project its beam upwardly, it is preferable to position it horizontally and use the sliding mirror. This produces a more compact unit, avoids movement of the laser itself, and avoids possible damage to the laser from any spillage from the lens container.

The turntable 3 permits the user to rotate the lens through ninety degrees, if analysis of the lens is desired in two planes. Operation of the turntable is manual in the preferred embodiment, although clearly that could be automated if desired.

A particular advantage of the invention is that it may be configured quite compactly within a readily portable case. The support surface 6 in the preferred embodiment is mounted across a base 40, and all mechanical and electrical parts other than the lens container 2, turntable 3, platform 4, and cameras 14, 16, can be located beneath the support surface 6. A lid 42 is positionable on the base, preferably sealed with a foam strip 43 to prevent ambient light from entering the case.

Lens Container

Figure 9:
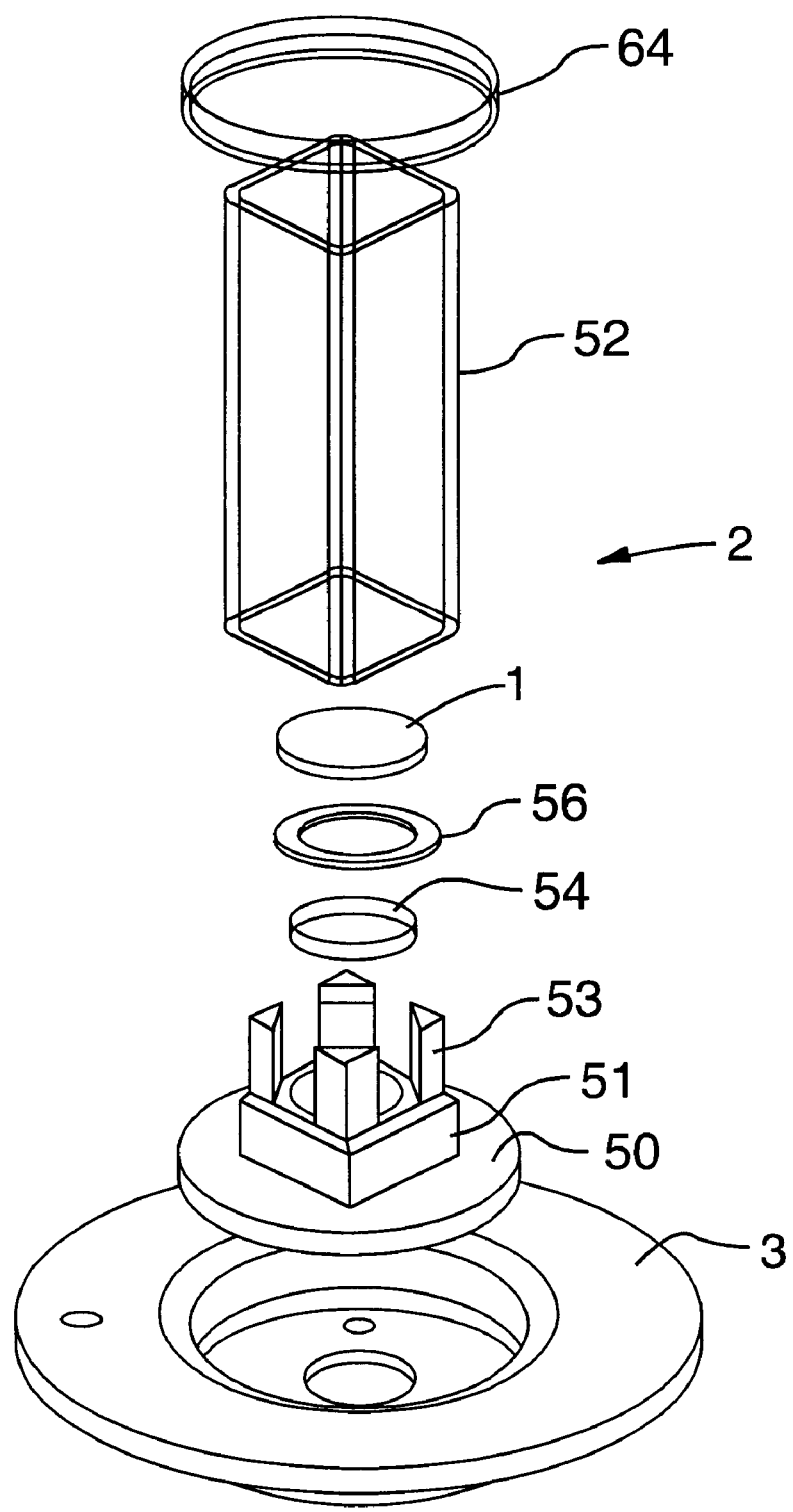
FIG. 9 is an exploded perspective view of the preferred embodiment of the lens container.
Figure 10:
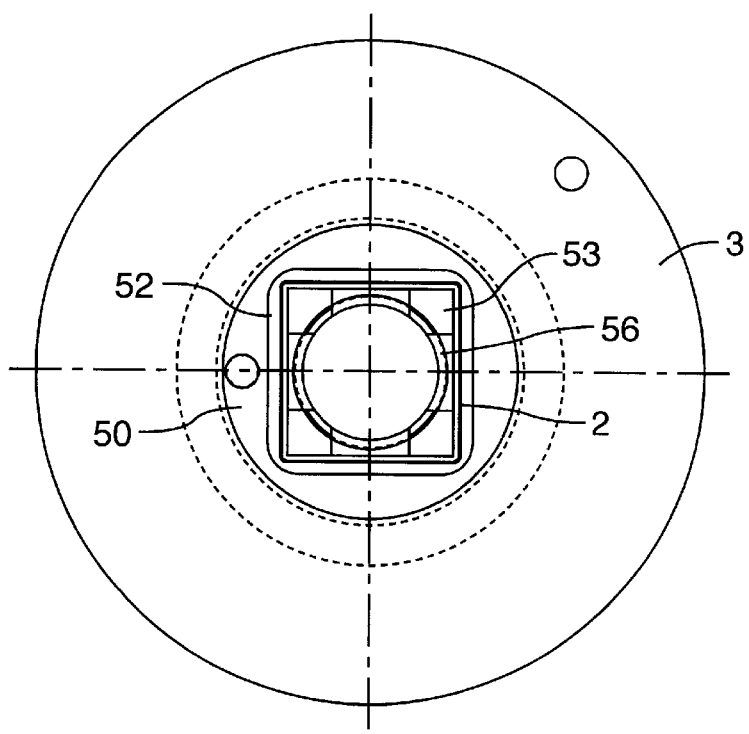
FIG. 10 is a top view of the lens container.
Figure 11:
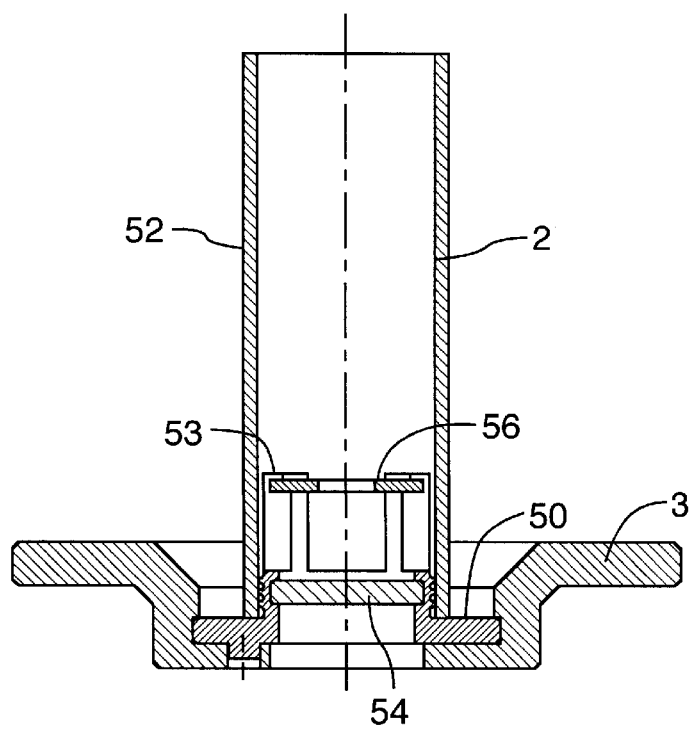
FIG. 11 is a cross-sectional elevation view of the lens container.

The lens container 2 will now be described in greater detail, with reference to FIGS. 9–11 in particular. The container has transparent side walls extending upwardly from a rubber base unit 50, forming a glass tube 52 with a square cross-section. The glass tube is sealed to the rubber base unit, by virtue of a tight fit over a correspondingly shaped upward projecting block portion 51 of the base unit. The base unit in turn seals into a recess in the turntable 3. A flat glass disk 54 is sealed across the inside of the block portion. The block portion has four corner posts 53 projecting upwardly therefrom. A lens seating washer 56 sits on notches on the corner posts, to support the lens 1. Washers with central openings of different diameters may be used for different diameter lenses.

To place a lens in the container so that it may be scanned, the glass tube 52 is removed from the base unit, the lens 1 is placed upon the washer 56. Once the lens is in place, the glass tube is placed over the lens and is pressed into place on the block portion 51, such that a liquid-tight seal is formed. Once this seal is formed, the culture medium is added to the container. Optionally a Petri dish 64 or other suitable cover is then placed atop the container to prevent bacteria and other contaminants from entering the tube. The lens container is oriented relative to the laser beam such that the laser beam is projected through the bottom transparent portion, then the lens, parallel to the lens optical axis. The central transparent portion of the container is aligned with the field of view of the cameras, with the flat sidewalls of the glass tube 52 facing directly at the cameras, in order to minimize the refraction effects while looking through the sidewalls.

Data Capture and Analysis

Using the apparatus of the invention, the method could be carried out using prior art analysis techniques such as those described in the Gershon et al. prior art. However, it is preferable to used the advanced analysis techniques described below, which are embodied in software.

As the laser is stepped across the lens after being suitably aligned (whether with the aid of an alignment camera 16 or otherwise), the actual position and slope of each beam is captured by the analysis camera 14. When all steps across the lens have been made, the captured data for each step position is used to calculate the back vertex distance of each position and the differences in that measurement at various positions, as well as the equivalent focal length. This procedure eliminates the need for the iterative pre-processing step used in the prior art Gershon et al. apparatus.

The nature of the data which is retrieved from the analysis camera is as follows:

Preferably, the analysis camera focuses incoming light onto a semiconductor wafer that is structured as an array of light sensitive elements or pixels. In the preferred embodiment, the camera has an array 320 pixels wide by 240 pixels high. Each pixel, when exposed to light, accumulates a voltage proportional to the amount of light striking that pixel. The circuits within the camera later extract the voltage on each pixel in turn and convert them into digital values from zero (0), for a dark pixel, to two hundred and fifty five (255) for a brightly lit pixel.

The camera outputs its data one line of pixels at a time. That is, in order to read the whole image the controller board must retrieve 240 lines of 320 pixels. That is, in order to process an entire image a total of 76,800 pixels must be retrieved.

Figure 12:
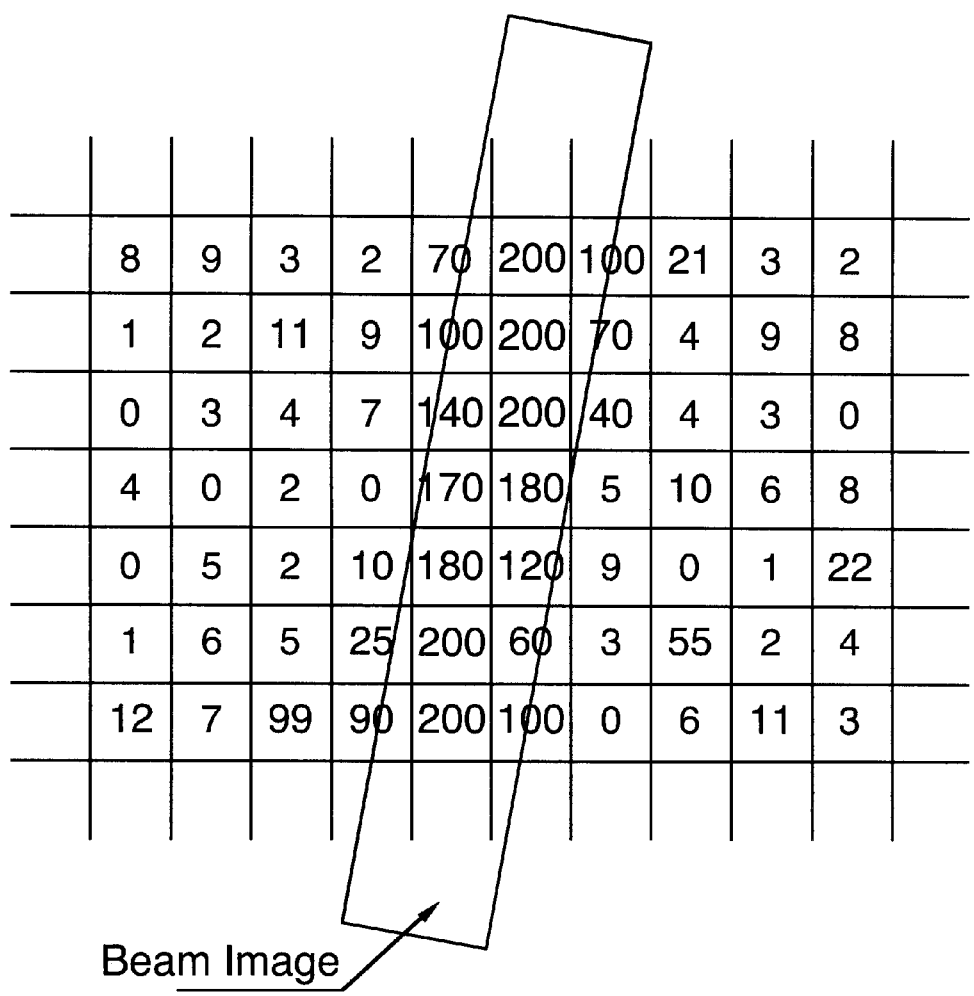
FIG. 12 is a typical image array viewed from the analysis camera, normal to the lens axis.

For operation of the preferred embodiment, only a subset of these data need to be transferred to the program. FIG. 12 shows a section of the camera image array that is typically encountered while looking for a laser beam. The image of the laser beam is projected onto the camera array. This causes a few pixels to have a significantly higher value than those outside the beam. Some pixels apparently outside the beam also occasionally have values that are alarmingly high. These may be caused by internal reflections in the camera, sparkles in the lens fluid, or flaws in the camera matrix. The software accounts for this phenomenon by preprocessing the data within the scanner during line-finding operations. Instead of transmitting the whole image array to the processing application, the microprocessor within the scanner bed examines each line as it receives it from the camera and detects where the brightest pixel is on that line. It then transmits only the relative pixel location on the line and the brightness at that point to the application.

Further preprocessing defined as the "sum of line" occurs during the operation to define back vertex locations along the lens. It involves analysing each line of the image from the top to the bottom. Looking at each line of the image from top to bottom where the image of the beam hits the camera array, the majority of the lines have a narrow bright spot. However, when the lens itself comes into view, the laser brightness spreads at the lens surface, causing the lens surface to "light up", permitting location of the back vertex. The software uses this characteristic to perform another preprocessing simplification. When in this mode the microprocessor retrieves and sums every pixel on each line and returns that sum for each line The application program uses the back vertex of the lens as the reference plane from which the focal length of each beam is calculated. When a scan is started by the user the software uses the scanner to determine the location of this point.

The scanner is first commanded to position the laser in the nominal center of the lens. The laser is then turned on and the scanner is commanded to provide the application with "sum of line" data. That is, the scanner causes the camera to capture a frame and retrieves the data from the camera, summing the pixels for each line and returning those sums to the application.

The application then calculates a differential curve for all of the data. This differential generates a peak value at the point where the back vertex of the lens comes into view. The program then remembers this location for later calculation and uses it as the lowest point to search for lines in the line finder.

Additionally, the routine also examines the upper part of the frame looking for bright spots in the top of the lens holder. This information is used to set the upper field of view for the line finder. When the back vertex and field of view has been determined the application then starts the scan sequence. The first step is to find the centerline of the camera. This line or beam is present at the start since the laser was already positioned to determine the back vertex distance. This operation is performed to calculate the skew on the camera caused by manufacturing inconsistencies. This value is later used to adjust the beam data. Having examined the centerline the laser is offset to the side of the lens by half of the scanning distance across the lens as chosen by the user.

The beam location and angle is determined, then the laser repositioned by the step size and the sequence repeated. Once all steps have been measured, the beam data is processed to determine the focal length of each beam relative to the back vertex, the average focal length and standard deviation and error of the mean. Additionally, similar results for the relative intensity of the beam are also calculated.

The critical element of the scanning software is the line finder algorithm. These routines are responsible for determining the location and angle of the beam. The routine examines the data retrieved from the scanner. This data is in the form of maximum pixel per line. That is, for every line in the field of view, the scanner returns the relative location of the brightest pixel and its intensity. The line finder stores this information in an array and scans through this array in an attempt to sanitize the results.

Since noise or bright spots in the fluid can cause some lines to be incorrectly reported, the line finder must examine each line with respect to the rest to determine if the data for that line is consistent. If it is not, then the routine attempts to relocate the data for that line within range of the rest. This technique significantly improves the ability to detect lines in noisy data. Once sufficient cleaning is done to the data the routine examines the data again and groups successive data that appear to be on a line into segments, The slope and position of each segment is computed. If multiple segments are found, each is compared with the other to determine if they fall on the same extrapolated line. If they do the line segments are joined to form a single line.

At the end of this process a single line will have been identified (if possible). The line data is then converted to metric measurements using the pre-calibrated scale of the camera.

After the scan data has been retrieved certain post processing activities take place to compensate for errors in the system. First the skew of the camera is removed by rotating the data an amount equal to but in the other direction to the skew of the centerline measured at the start of the scanning process. Next, and if enabled by the user, The software attempts to shift the data relative to the center of lens to such that the average focal length of all beams to the left of center match those to the right of center. This operation corrects for slight errors in initial positioning.

Because of inconsistencies and inaccuracies in the construction of the scanner and the cameras themselves, the scanner and application software are required to adjust the data to compensate for these errors. The application uses information that is stored in non-volatile memory within the scanner itself. This information is loaded into the device by running the calibration program that ships with the unit.

The invention includes the further procedure of applying a stimulus to the lens in the culture medium, waiting a period of time, further projecting a laser beam through the lens at different positions across the lens and repeating the above steps and then comparing the focal length, focal length variance (spherical aberration) and transparency of the lens before and after that period of time, so as to determine the irritancy of the lens to the stimulus.

It will be appreciated that the above description relates to the preferred embodiment by way of example only. Many variations on the invention will be obvious to those knowledgeable in the field, and such obvious variations are within the scope of the invention as described and claimed, whether or not expressly described.

What is claimed as the invention is:

1. Apparatus for evaluation of focal characteristics and transparency of vertebrate eye lenses, said apparatus comprising:
   a transparent lens container arranged to support a said lens horizontally with the axis of the lens vertical;
   a laser arranged to project a vertical laser beam through said lens;
   means for moving said vertical laser beam horizontally across said lens in a first horizontal direction;
   one and only one analysis camera facing said lens and lens container in a second horizontal direction at right angles to said first horizontal direction, whereby an image of said laser beam may be captured as it passes through said lens at different horizontal points across said lens; and
   alignment means for aligning said lens in said second horizontal direction, relative to said laser beam.

2. Apparatus as recited in claim 1, wherein said laser is mounted horizontally and wherein said laser beam is directed upwardly via a mirror after leaving said laser, said means for moving said laser beam horizontally comprising a mechanism for moving said mirror horizontally.

3. Apparatus as recited in claim 1, wherein said alignment means comprises a manual adjustment of the position of said lens container relative to said laser beam, and an alignment camera faxing said lens and said lens container in said first horizontal direction to display an image of said laser beam passing through said lens, whereby said the position of said lens may be adjusted to align the lens axis with said laser beam.

4. Apparatus as recited in claim 1, wherein said lens container in mounted on a horizontal turntable such that it and a lens carried in it may be rotated in a horizontal plane.

5. Apparatus as recited in claim 1, wherein said lens container comprises transparent side walls extending upwardly from a rubber base unit, forming a glass tube with a square cross-section, said glass tube being sealed to said rubber base unit by virtue of a tight fit over a correspondingly shaped upward projecting block portion of said base unit, said block portion having four corner posts projecting upwardly therefrom, having means for supporting a washer having a central opening, whereby a lens may be supported on said washer across said central opening.

6. Apparatus as recited in claim 1, all mounted within a case, said case having a support surface mounted across a base, with said lens container and analysis camera mounted on said support surface, said case having a lid positionable on the base and sealable thereto to prevent ambient light from entering the case.

7. Apparatus as recited in claim 6, where said lens container is mounted on a turntable on a slidable platform on said support surface, wherein said alignment means comprises an adjustment means for repositioning said slidable platform relative to said support surface.

8. Apparatus as recited in claim 6, wherein said laser is mounted horizontally beneath said support surface and wherein said laser beam is directed upwardly via a mirror after leaving said laser, through an opening in said support surface, said means for moving said laser beam horizontally comprising a motor mounted beneath said support surface, connected to move a slidable carriage carrying said mirror.

9. Apparatus as recited in claim 7, wherein said laser is mounted horizontally beneath said support surface and wherein said laser beam is directed upwardly via a mirror after leaving said laser, through an opening in said support surface, said means for moving said laser beam horizontally comprising a motor mounted beneath said support surface, connected to move a slidable carriage carrying said mirror.

10. A method for evaluation of focal characteristics and transparency of vertebrate eye lenses comprising the steps of:
   a. positioning a said lens in a culture medium within a transparent lens container, said lens and said container being positioned for viewing by one and only one analysis camera directed at said lens and said container at an angle substantially normal to the lens axis;
   b. projecting a laser beam through said lens, parallel to the optical axis of said lens, at a plurality of positions across said lens;
   c. measuring the intensity and directional path of said laser beam after it has exited from the lens and measuring the back vertex location of said lens, at said plurality of positions along the lens; and
   d. analysing said measured intensity and directional path of said laser beam and said back vertex location at said plurality of positions for determination of focal length, focal length variance (spherical aberration) and transparency of said lens.

11. A method as recited in claim 10, comprising the further step, after step a., of aligning said lens such that said plurality of positions across said lens will be aligned approximately with the lens axis.

12. A method as recited in claim 10, comprising repeating steps b. to d. after a period of time, to evaluate changes overtime in response to a stimulus applied to said lens.

* * * * *